US010379060B2

(12) United States Patent
Cho et al.

(10) Patent No.: US 10,379,060 B2
(45) Date of Patent: Aug. 13, 2019

(54) APPARATUS FOR MAKING ARTIFICIAL ATMOSPHERIC ENVIRONMENT INCLUDING DUST AND ANALYSIS SYSTEM FOR DUST-BLOCKING OF COSMETICS USING THE SAME

(71) Applicant: COSMECCA KOREA CO., LTD., Chungcheongbuk-do (KR)

(72) Inventors: Hyun Dae Cho, Cheongju-si (KR); Hyoun Cheol An, Cheongju-si (KR); Byoung Moon Kim, Suwon-si (KR); Hong Seok Son, Yongin-si (KR); Bong Jun Kim, Yongin-si (KR); Young Min Kim, Jecheon-si (KR)

(73) Assignee: COSMECCA KOREA CO., LTD., Chungcheongbuk-Do (KR)

( * ) Notice: Subject to any disclaimer, the term of this patent is extended or adjusted under 35 U.S.C. 154(b) by 112 days.

(21) Appl. No.: 15/533,906

(22) PCT Filed: May 30, 2016

(86) PCT No.: PCT/KR2016/005710
§ 371 (c)(1),
(2) Date: Jun. 7, 2017

(87) PCT Pub. No.: WO2017/164457
PCT Pub. Date: Sep. 28, 2017

(65) Prior Publication Data
US 2018/0059030 A1    Mar. 1, 2018

(30) Foreign Application Priority Data
Mar. 24, 2016    (KR) .................. 10-2016-0035231

(51) Int. Cl.
*G01N 21/94*    (2006.01)
*F24F 13/28*    (2006.01)
(Continued)

(52) U.S. Cl.
CPC ............ *G01N 21/94* (2013.01); *A61Q 17/00* (2013.01); *A61Q 19/00* (2013.01); *B08B 15/02* (2013.01);
(Continued)

(58) Field of Classification Search
CPC .... G01N 21/94; G01N 17/002; G01N 1/2226; G01N 1/24; G01N 17/00; G01N 1/22;
(Continued)

(56) References Cited

U.S. PATENT DOCUMENTS

2004/0158121 A1* 8/2004 Ford ..................... B08B 15/026
600/21

FOREIGN PATENT DOCUMENTS

JP    H03-011718    *  3/1991
JP    H03-011718 Y2    3/1991
(Continued)

OTHER PUBLICATIONS

International Search Report (ISR) dated Dec. 21, 2016, for PCT/KR2016/005710.

*Primary Examiner* — Siamak Harandi
(74) *Attorney, Agent, or Firm* — Bacon & Thomas, PLLC (57) ABSTRACT

An apparatus for making artificial atmospheric environment and analysis system for dust-blocking of cosmetics using the same, and the apparatus for making artificial atmospheric environment includes a chamber in which fine dust is made; a wind generation unit including a plurality of driving fans disposed inside the chamber having different angles, the wind generation unit moving supplied dust inside the chamber so that the dust is distributed as actual atmospheric environment in the same or similar manner; and a dust supply unit which is provided integrally with or separately from the chamber to supply fine dust to the chamber, and the analysis system for dust blocking of cosmetics using the apparatus for making artificial atmospheric environment.

20 Claims, 6 Drawing Sheets (51) Int. Cl.
  *F24F 11/00*   (2018.01)
  *G01N 1/22*    (2006.01)
  *G01N 1/24*    (2006.01)
  *G01N 17/00*   (2006.01)
  *A61Q 17/00*   (2006.01)
  *A61Q 19/00*   (2006.01)
  *B08B 15/02*   (2006.01)
  *F24F 13/08*   (2006.01)
  *G01N 21/88*   (2006.01)
  *A61B 5/00*    (2006.01)
  *G01N 1/00*    (2006.01)

(52) U.S. Cl.
  CPC ............ *F24F 11/00* (2013.01); *F24F 13/081* (2013.01); *F24F 13/28* (2013.01); *G01N 1/22* (2013.01); *G01N 1/2226* (2013.01); *G01N 1/24* (2013.01); *G01N 17/00* (2013.01); *G01N 17/002* (2013.01); *G01N 21/8851* (2013.01); *A61B 5/441* (2013.01); *G01N 2001/002* (2013.01); *G01N 2001/2241* (2013.01)

(58) Field of Classification Search
  CPC ..... G01N 2001/002; G01N 2001/2241; A61Q 19/00; A61Q 17/00; B08B 15/02; F24F 13/081; F24F 11/00; A61B 5/441
  See application file for complete search history.

(56) References Cited

FOREIGN PATENT DOCUMENTS

| | | |
|---|---|---|
| JP | H10-038790 A | 2/1998 |
| JP | 2011-257178 A | 12/2011 |
| KR | 10-1997-0001969 B1 | 2/1997 |
| KR | 20-0096448 | 9/2006 |
| KR | 10-1203222 B1 | 11/2012 |
| KR | 10-2016-0014996 A | 2/2016 |

* cited by examiner

APPARATUS FOR MAKING ARTIFICIAL ATMOSPHERIC ENVIRONMENT INCLUDING DUST AND ANALYSIS SYSTEM FOR DUST-BLOCKING OF COSMETICS USING THE SAME

BACKGROUND OF THE INVENTION

Field of the Invention

The present invention relates to a system for analyzing dust-blocking of cosmetics using an apparatus for making artificial atmospheric environment including fine dust, and more particularly to, an apparatus for making artificial atmospheric environment including fine dust which is configured to form artificial atmospheric environment which is similar to pollution level of fine dust of external atmospheric environment, and an analysis system of dust-blocking of cosmetics using the apparatus by measuring remaining fine dust of an area where the cosmetics are applied.

BACKGROUND OF THE RELATED ART

Fine dust refers to dust which is very tiny and hard to be seen by naked eyes of a human. Fine dust having a diameter of 10 μm (1 m/1 million) is floating and scattering on air for a long time. Diameter of fine dust which is equal to or less than 10 μm is categorized as ultrafine dust of which diameter is equal to or less than 2.5 μm (1/30 of diameter of hair). Fine dust is mostly filtered at nose but ultrafine dust is not filtered at nose or airway during breathing, and it can be attached to lung through bronchial tubes or penetrated deep into pores of the skin.

In such fine dust, fine dust (30~50%) from China due to fossil fuels used for industry is combined with pollutants (50~70%) which is generated from automobiles • factories • households, containing heavy metal material such as aluminum, copper, cadmium, and lead. When exposed to ultrafine dust, immunity drastically worsens, making people vulnerable to respiratory disease including cold, asthma, bronchial trouble and other diseases such as cardiovascular disorder, skin disorder, and eye problems, or the like.

In particular, ultrafine dust or high-concentration fine dust is easily attached to the skin, and absorbed deep into pores, causing skin troubles or serious irritation to skin. Therefore, it is necessary to come up with a way to protect the skin from fine dust including pollutants floating in the air in order to keep healthy life under the clean living environment.

With respect to the above, there have been developed various cosmetics having a function to block fine dust, but no apparatus which may conveniently measure and analyze fine dust-blocking effect of cosmetics under the actual atmospheric environment has been developed.

PRIOR ART DOCUMENT (Patent document 1) Korean Registered Patent Publication No. 10-1203222
(Patent document 2) Registered Utility Model Publication No. 20-0096448

SUMMARY OF THE INVENTION

Therefore, the present invention has been made to solve the above-mentioned problems occurring in the prior arts, and it is an object of the present invention to provide an apparatus for making artificial atmospheric environment including fine dust which is configured to form artificial atmospheric environment similar to pollution level of fine dust of external atmospheric environment, and an analysis system of dust-blocking of cosmetics using the apparatus by measuring remaining fine dust of an area where the cosmetics are applied, in order to measure and analyze how much fine dust the cosmetics may block by using an amount of remaining fine dust in an area of a subject where the cosmetics are applied.

In order to accomplish the above object, according to one exemplary embodiment of the present invention, there is provided an apparatus for making artificial atmospheric environment including dust.

The apparatus for making artificial atmospheric environment includes:
a chamber 10 in which fine dust is made;
a wind generation unit 20 including a plurality of driving fans 21, 22, 23, 24 disposed inside the chamber 10 having different angles, the wind generation unit moving supplied dust inside the chamber 10 so that the dust is distributed as actual atmospheric environment in the same or similar manner; and
a dust supply unit 30 which is provided integrally with or separately from the chamber 10 to supply fine dust to the chamber 10.

Also, the apparatus further comprises a filter 40 having a backflow prevention filter which prevents air flow from inside to outside the chamber 10, but allows airflow from outside to inside the chamber 10.

In the apparatus, the chamber 10 is formed with an insertion hole 12 to insert arms of a subject on one side, an inlet 14 through which dust is inserted on an upper portion of an upper surface or a side surface, and an outlet 16 at a bottom of a side surface or a lower portion.

In the apparatus, the insertion hole 12 of the chamber 10 comprises a sealing member to present outflow of fine dust to outside the chamber 10, and the chamber formed with the insertion hole 12 further comprises a support member 18 to hold arms of a subject.

In the apparatus, the chamber 10 is made of transparent or semi-transparent acrylic plate.

Also, the plurality of driving fans 21, 22, 23, 24 of the wind generation unit 20 comprises:
a corner driving fan 21 disposed at each corner of a bottom surface of the chamber 10;
a side lower driving fan 22 disposed inward from a bottom surface of facing side surfaces of the chamber 10;
a central driving fan 23 disposed at a center of a bottom surface of the chamber 10; and
a side upper driving fan 24 disposed at a central portion or an upper portion of facing side surfaces of the chamber 10.

In the apparatus, the corner driving fan 21 is disposed at a bottom surface of rectangular corners inside the chamber 10 diagonally to face with each other, and a front direction of the fan is set aside from a central reference point.

In the apparatus, the corner driving fan 21 comprises a first corner driving fan 21a, a second corner driving fan 21b, a third corner driving fan 21c, and a fourth corner driving fan 21d disposed at a direction in which a front direction of each fan is rotated by 1~15° (θ1) with reference to a center of the chamber 10.

In the apparatus, the side lower driving fan 22 is disposed such that a front surface of a fan is disposed to opposite to each other at both sides of the same bottom surface adjacent to a pair of side portions facing each other, and comprises a first side lower driving fan 22a and a second side lower driving fan 22b disposed at a direction rotated by 1~7° (θ2) with reference to a vertical connection line which connects a pair of side portions of the chamber 10 and a central reference point.

In the apparatus, the central driving fan 23 is disposed such that a front surface of a fan is placed upward at a center of a bottom surface of the chamber 10 and the fan is disposed to be apart from the bottom surface.

In the apparatus, the central driving fan 23 comprises a first central driving fan 23a and a second central driving fan 23b which are disposed to be apart from each other at a predetermined distance.

In the apparatus, the central driving fan 23 generates convection, inhales dust at a bottom portion, and sends dust to an upper portion.

In the apparatus, the side upper driving fan 24 is disposed such that a front surface of a fan is disposed to be opposite to each other at a pair of central or upper portions facing with each other of the chamber 10, and comprises a first side upper driving fan 24a and a second side upper driving fan 24b disposed at a direction rotated by 1~50° (θ3) with reference to a vertical connection line which connects a pair of side portions of the chamber 10 and a central reference point.

In the apparatus, the dust supply unit 30 comprises carbon black as a material of the fine dust.

Also, according to one exemplary embodiment of the present invention, there is provided an analysis system for dust blocking of cosmetics using an apparatus for making artificial atmospheric environment.

The system comprises:

a capturing device 100 which captures a target which is applied with cosmetics and a target which is not applied with cosmetics before and after exposure to fine dust;

an apparatus 1 for making artificial atmospheric environment which exposes the target to fine dust, the apparatus comprising anyone of claim 1 to claim 14; and an image analysis device 200 which compares and analyzes images of the targets captured before and after exposure to fine dust.

In the system, the apparatus 1 drives each driving fan provided inside the chamber for 20-40 seconds, and wherein carbon black is input in an environment where wind speed is kept to 2.5~3 m/s, and concentration of fine dust by the carbon black is 200~3,000 mg/m3.

In the system, the analysis device 200, which is interlocked with the capturing device 100, receives images captured before and after exposure to fine dust through an image receiving unit, converts the received images to an editable image file thorough a conversion unit, and measures and analyzes fine dust amount from the converted image file.

In the system, the analysis device 200 applies counting statistics to measure and analyze the fine dust amount, reach measurement results by setting an intensity range, and analyze an intensity range by overlapping a same part between a part before exposure and a part after exposure.

By using the apparatus for making artificial atmospheric environment including fine dust, the present invention has the effect to efficiently measure and analyze how much fine dust the cosmetics applied to a subject may block.

BRIEF DESCRIPTION OF THE DRAWINGS

Further objects and advantages of the invention can be more fully understood from the following detailed description taken in conjunction with the accompanying drawings in which:

FIG. 5 is image date illustrating changes in remaining fine dust of a part where cosmetic is applied and a part where cosmetic is not applied (5 images selected from 20)

DETAILED DESCRIPTION OF THE PREFERRED EMBODIMENT

The preferred embodiments of the invention will be hereinafter described in more detail with reference to the accompanying drawings.

Figure 1:
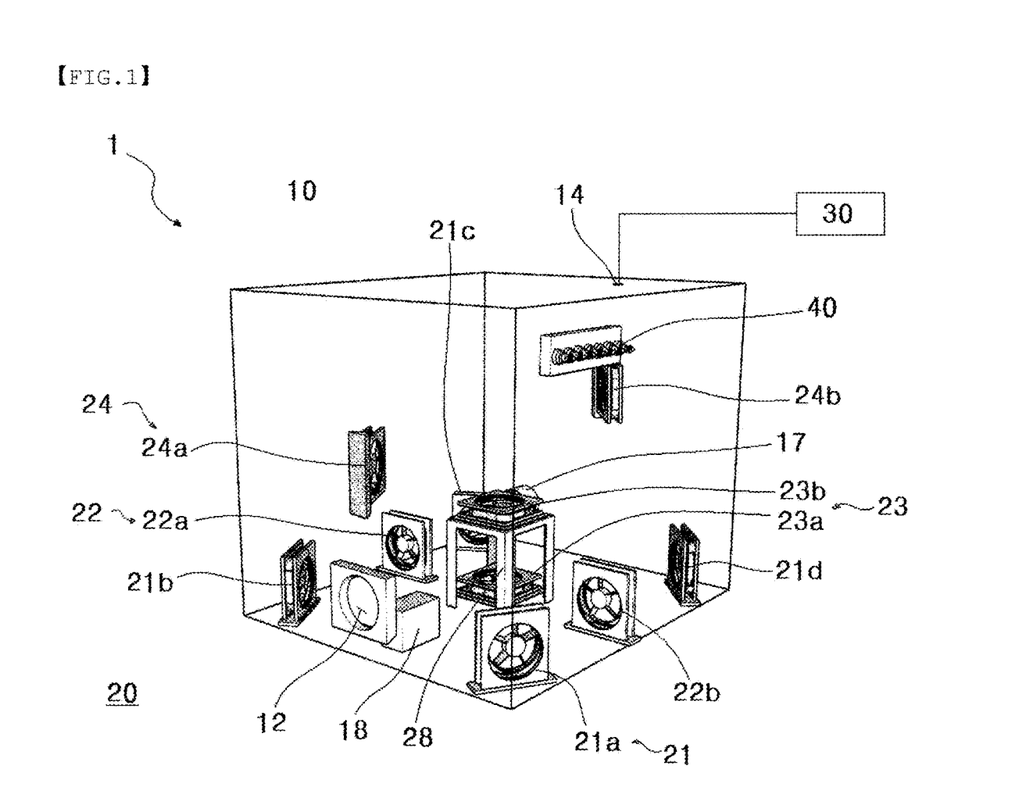
FIG. 1 is a schematic configuration diagram of an apparatus for making artificial atmospheric environment including dust according to a preferred embodiment.
Figure 2:
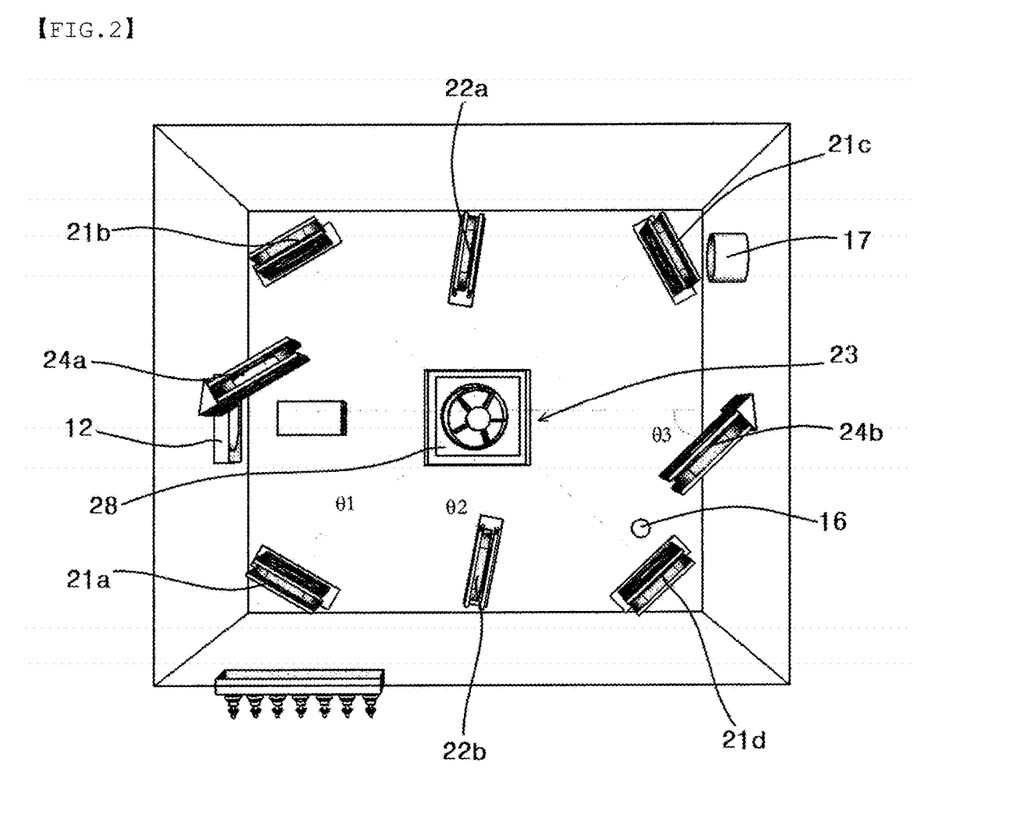
FIG. 2 is a floor plan of FIG. 1.
Figure 3:
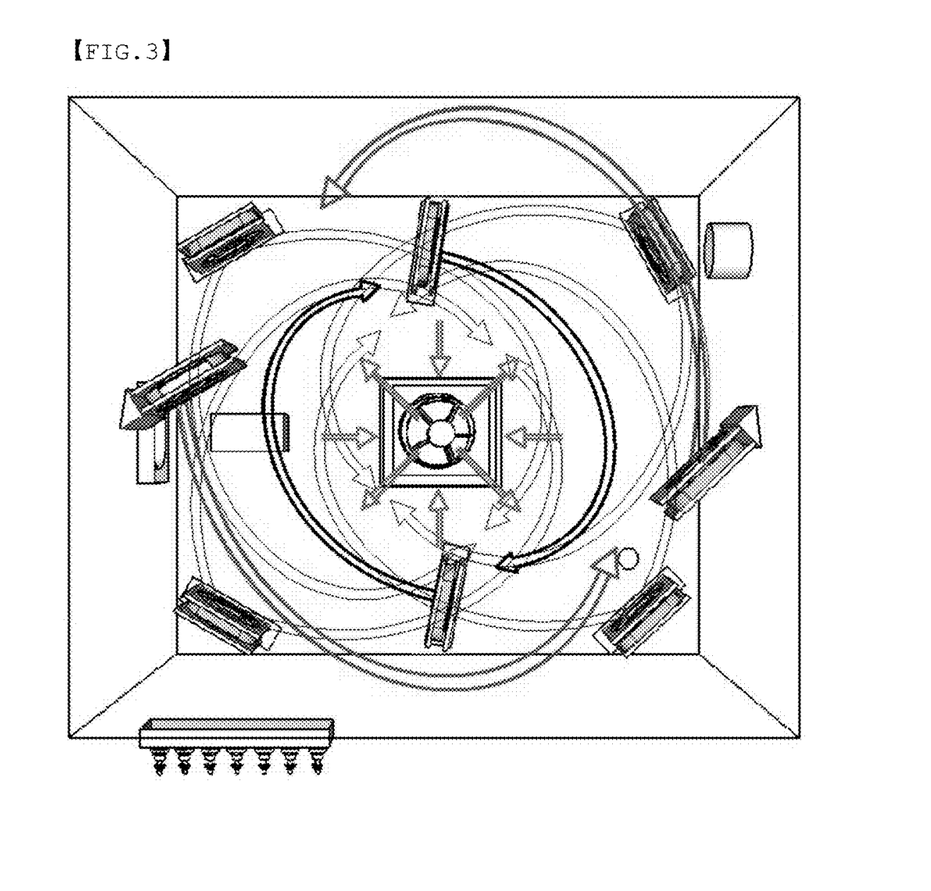
FIG. 3 is a schematic view of movement, flow, and distribution of fine dust by the wind generation device provided in the chamber of FIG. 1.
Figure 4:
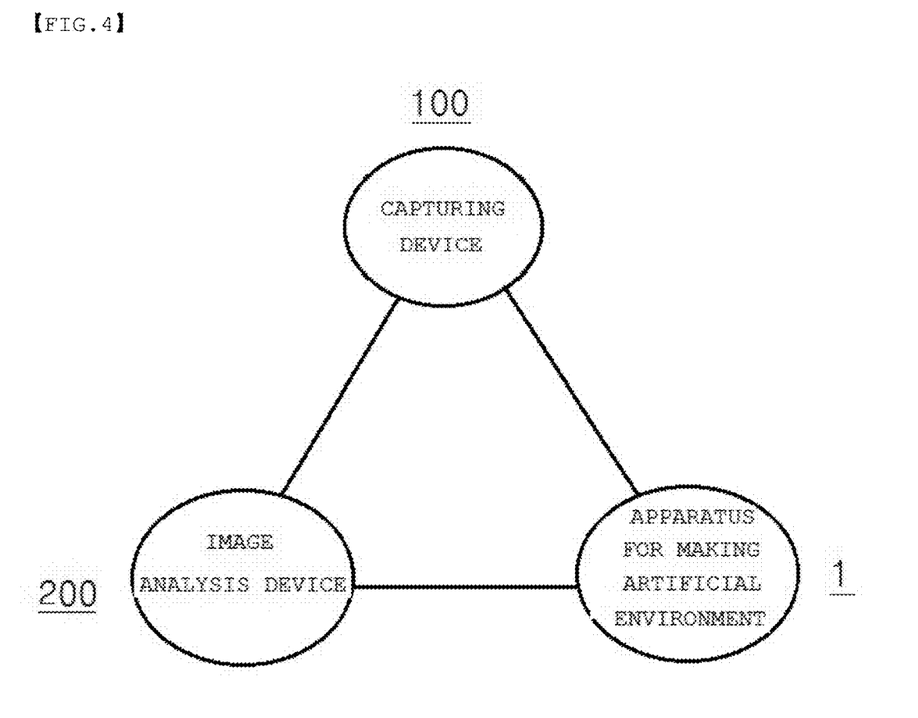
FIG. 4 is a schematic configuration diagram of analysis system for dust-blocking of cosmetics using the apparatus for making artificial atmospheric environment including dust according to the preferred embodiment.
Figure 6:
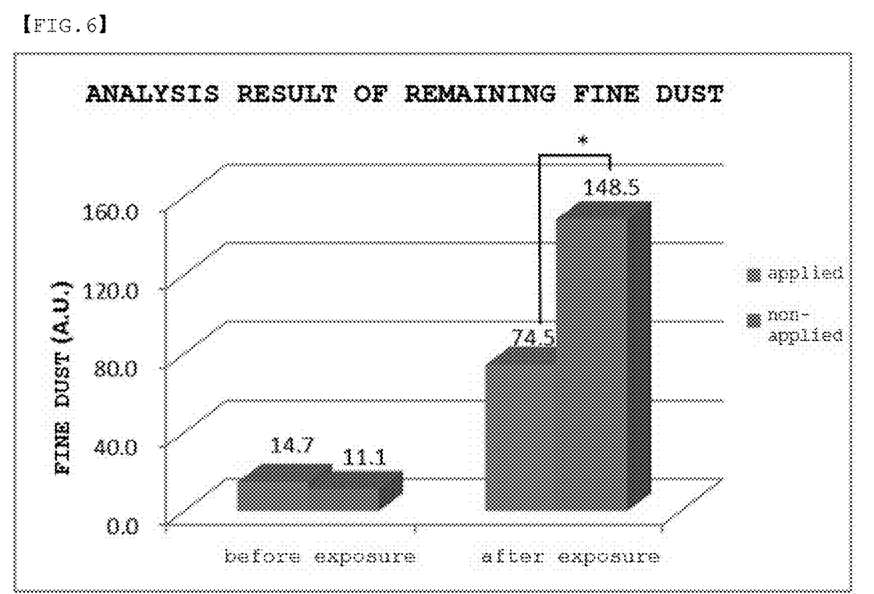
FIG. 6 is a diagram indicating analysis results before and after exposure to fine dust.

FIG. 1 is a schematic configuration diagram of an apparatus for making artificial atmospheric environment including dust according to a preferred embodiment, FIG. 2 is a floor plan of FIG. 1, FIG. 3 is a schematic view of movement, flow, and distribution of fine dust by the wind generation device provided in the chamber of FIG. 1, FIG. 4 is a schematic configuration diagram of analysis system for dust-blocking of cosmetics using the apparatus for making artificial atmospheric environment including dust according to the preferred embodiment, FIG. 5 is image date illustrating changes in remaining fine dust of a part where cosmetic is applied and a part where cosmetic is not applied (5 images selected from 20), and FIG. 6 is a diagram indicating analysis results before and after exposure to fine dust.

As illustrated in FIGS. 1 to 3, an apparatus 1 for making artificial atmospheric environment including fine dust according to the preferred embodiment includes a chamber 10, a wind generation unit 20, a dust supply unit 30, and a filter 40.

The chamber 10 is an airtight case where fine dust is made. At a lower portion of one side of the chamber, an insertion hole 12 to insert arms of a subject is formed, and at an upper surface or a side surface of a side, an inlet 14 through which dust is inserted is formed. Also, at a bottom of a side surface or a lower portion of the chamber 10, an outlet 16 is formed so that waste water from water cleaning to remove fine dust within the chamber after a test is done can be drained. In addition, a connection 17 to which a vacuum clear may be inserted to inhale fine dust inside the chamber can be further included.

A sealing member (not shown) to prevent outflow of dust during test process may be included so that a part excluding arms of the subject may be closed. In addition, inside the chamber where the insertion hole 12 of the chamber 10 is formed, a support member 18 to hold arms of the subject can be further included.

It is desirable that the chamber 10 is made of transparent or semi-transparent acrylic plate so that the chamber may be seen from outside. Through this, a state of removing fine dust during the test process can be easily checked. Semi-transparent material or opaque material can be used.

The wind generation unit 20 makes dust which is inserted through the insertion hole 14 flow inside the chamber 10 so that dust is distributed in an entire space of the chamber 10 in the same or similar manner as actual atmospheric environment. The wind generation unit may include a plurality of driving fans 21,22,23,24, that is, a corner driving fan 21 disposed at each corner of a bottom surface of the chamber, a side lower driving fan 22 disposed inward from a bottom surface of facing side surfaces, a central driving fan 23 disposed at a center of a bottom surface, and a side upper driving fan 24 disposed at a central portion or an upper portion of facing side surfaces of the chamber. Each driving fan of the wind generation unit 20 is connected to power source (not shown) which rotates a fan.

Here, the corner driving fan 21 is disposed at a bottom surface of rectangular corners inside the chamber diagonally to face with each other, and includes a first corner driving fan 21a, a second corner driving fan 21b, a third corner driving fan 21c, and a fourth corner driving fan 21d disposed at a direction in which a front direction of each fan is rotated by 1~15° (θ1), preferably 5~10°, with reference to a center of the chamber 10.

In this case, the first driving fan 21a is rotated to face the second corner driving fan 21b, the second corner driving fan 21b is rotated to face the first corner driving fan 21a, the third corner driving fan 21c is rotated to face the second corner driving fan 21b, and the fourth corner driving fan 21d is disposed toward the third corner driving fan 21c, but is relatively small compared to other corner driving fans having different rotation degrees.

As such, disposition and rotation degrees of the corner driving fan 21 is to evenly distribute fine dust inside the chamber under wind speed of 2.5~3 m/s, and if exceeding the aforementioned disposition state or numerical range, inserted dust does not move and gather together, failing to form dust distribution having the same concentration of the actual atmospheric environment.

Also, a fan of the corner driving fan is provided such that a front direction of the corner driving fan is set aside from a central reference point, and dust moves to a side area instead of diagonal direction passing the central reference point along with air flow (navy line of FIG. 3) by wind which is out from each driving fan. At the same time, a direction changes by wind which is out from an adjacent corner driving fan and consequently, each dust rotates around the central reference point.

The side lower driving fan 22 is disposed such that a front surface of a fan is disposed to be opposite to each other at both sides of the same bottom surface adjacent to a pair of side portions facing each other, and this fan includes a first side lower driving fan 22a and a second side lower driving fan 22b disposed at a direction rotated by 1~7° (θ2) with reference to a vertical connection line which connects a pair of side portions of the chamber 10. Air flow generated by wind which is out from the side lower driving fan 22 is indicated in black line as illustrated in FIG. 3.

The first corner driving fan 21a, the second corner driving fan 21b, the third corner driving fan 21c, and the fourth corner driving fan 21d are configured such that size is different or gradually different, and the first side lower driving fan 22a and the second side lower driving fan 22b are also configured to be different in size or height so that dust is rotated spirally to move upward.

In addition, disposition and rotation angle of the side lower driving fan 22 are designed so that fine dust is not piled at a bottom of the chamber and rotates at a lower portion of the chamber to be evenly distributed by interacting with the corner driving fan under the wind speed of 2.5~3 m/s. If exceeding the disposition state or the numerical range, the input dust is driven into a corner of the chamber or a side where a bottom is in contact with a side portion and dust is piled. The dust does not rotate and gather at a place and dust distribution in the same manner as actual atmospheric environment is not formed.

The central driving fan 23 is designed such that at least two fans are placed upward at a center of a bottom surface, the first central driving fan 23a and the second central driving fan 23b are disposed to be apart from each other at a predetermined distance, and the first central driving fan 23a at a lower portion is placed to be apart from the bottom. At this time, the first central driving fan 23a and the second central driving fan 23b may be disposed using a loading frame 28 which is an auxiliary tool.

The central driving fan 23 inhales dust which sinks at a bottom by gravity and sends dust to upward, causing convection to move air and dust from downside to upside so that dust can float. It is desirable that a rotation direction of a fan is designed so that dust is inhaled from a lower side and emitted at an upper side. Air flow which is indicated as convection by wind which comes from the central driving fan 23 toward a front side is indicated in green line in FIG. 3.

In the present invention, it is illustrated that two central driving fans 23 are disposed, but it is not limited thereto, and there may be one or a plurality of driving fans which are placed to be apart from each other.

The side upper driving fan 24 is disposed at a center or upper part of a pair of facing side portions so that dust does not sink along with air flow and is distributed evenly. The side upper driving fan includes a first side upper driving fan 24a and a second side upper driving fan 24b which are disposed at a direction with reference to a vertical connection line which connects a pair of side portions of the chamber and a central reference point. At this time, the first side upper driving fan 24a and the second side upper driving fan 24b are disposed at a direction rotated by 1~50° (θ3), preferably 15~45°, with reference to a vertical connection line.

The side upper central driving fan 24 prevents moving downward of dust which is disposed at a central upper part of the chamber and dust sent to upside by convection of the central driving fan 23 by gravity and enables even distribution of dust within the chamber. Air flow generated by wind which comes out from the side upper driving fan 24 is indicated in a red line of FIG. 3.

At this time, it is desirable that the side upper driving fan 24 is disposed at a side of another pair of side portions which are different from side portions where the side lower driving fan 22 is disposed. This is purposed to prevent uniform rotation and floating of dust by distributing a reference point of rotation and floating of air to be different so that dust may be evenly distributed within the chamber.

In the present invention, two side upper driving fans 24 and side lower driving fans 22 are provided respectively and are disposed to cross each other, but it is not limited thereto. That is, four side upper driving fans and side lower driving fans may be provided respectively, and the side lower driving fan 22 may be placed on entire four sides of a bottom and the side lower driving fan 24 may be disposed on an entire portion of upper central part of four sides.

Air flow which is generated by the wind generation unit 20 is caused by interference that air flow is reinforced, offset, or change by each driving fan provided in the chamber and fine dust is distributed following the air flow.

The dust supply unit 30 includes dust or fine dust and supplies such dust to the chamber 10 through the inlet 14. As a material of the fine dust, a material having good absorbability such as carbon black is included. This is purposed to easily analyze an image of fine dust.

Also, as to an amount of fine dust supplied to the chamber in order to secure meaningful test results and relevant images, a numerical value which is higher than concentration of fine dust in air is used.

In the present invention, carbon black is used as a material of fine dust for testing is used, but it is not limited thereto and various materials can be used.

Detailed configuration of the dust supply unit 30 is not illustrated in the present invention, but it may be a device having an inside fan and fine dust which outputs fine dust to outside using an outlet or it may be a simple device made of a hopper and fine dust only.

The filter 40 includes a backflow prevention filter to prevent inside of the chamber being in a vacuum state during a cleaning process by inserting a vacuum cleaner through the connection tool 17 to remove fine dust inside the chamber 10, this prevents air flow from inside of the chamber to outside, and allows air flow from outside to inside.

It is desirable that water cleaning is available for removing fine dust in the chamber, and each driving fan maintains a driving state during the cleaning process. By driving of the driving fan, fine dust in an entire part of the chamber and fine dust attached to a driving fan may be completely removed.

According to a preferred embodiment of the present invention, analysis system for dust blocking of cosmetics using the apparatus for making artificial atmospheric environment may include a capturing device 100, an apparatus 1 for making artificial atmospheric environment, and an image analysis unit 200.

The capturing device 100 is a device which captures a target that is applied with cosmetics and a target which is not applied with cosmetics before and after exposure to fine dust. In order to detect an image for analysis of remaining fine dust, it is desirable that high resolution digital camera is used and capturing is performed in a clean air under constant temperature and humidity where constant lighting is installed.

Arms of the subject where a part is applied with cosmetics and another part is not applied with cosmetics are captured for two times under the same condition before and after the arms are exposed to fine dust. At this time, size of the part where cosmetic is and is not applied is 3 cm×3 cm respectively, and an amount of application of cosmetics is an area of the application of cosmetics×2 μg.

Also, in order to minimize errors of image analysis before and after capturing, capturing is performed after 15 minutes from application of cosmetics before exposure to fine dust, and even in case of exposure to fine dust, capturing is performed after 15 minutes in a clean area of constant temperature and humidity with constant lighting.

The apparatus 1 for making artificial atmospheric environment is formed with the aforementioned elements and exposes the capturing object to fine dust. The apparatus 1 drives each driving fan provided inside the chamber for 20~40 seconds, preferably 30 seconds, inserts carbon black through an inlet 14 in an environment where wind speed is kept to 2.5~3 m/s which is similar to actual atmospheric environment, and controls amount of carbon black so that concentration of fine dust by carbon black is 200~3,000 mg/m3 which is higher than concentration of actual air by 100~1,500 times, preferably 1,800 mg/m3 which is 900 times higher, for analysis of an image.

Arms of the subject are inserted through the insertion hole 12 at a side of the chamber to the aforementioned fine dust environment and exposed for 5~20 minutes, preferably 10 minutes.

Arms of the subject exposed to fine dust are captured through a capturing device, and each image captured before and after exposure to fine dust is sent to the analysis device 200.

The analysis device 200 is designed to compare and analyze images of the capturing object before and after exposure to fine dust and the analysis device is interlocked with the capturing device 100. The analysis device receives images captured before and after exposure to fine dust through an image receiving unit, converts the received images to an editable image file such as jpeg, and applies counting statistics to measure an amount of fine dust from the converted image file. The measurement result is drawn by setting an intensity range, and analyzed by overlapping the same part between a part before exposure and a part after exposure.

Here, as for numerical analysis, measurement results about changes in remaining fine dust of an area where cosmetics are applied and an area where cosmetics are not applied are analyzed using independent t-test. Also, it is considered that the static results have statistical significance when significance difference is 5% ($p<0.05$) which is mostly used in the area of biological statistics analysis.

ANALYSIS EXAMPLE

After applying cosmetics on arms of 20 subjects participating in this test and dividing areas of arms to an area where cosmetics are applied and an area where cosmetics are not applied, these arms are exposed to fine dust. By capturing these arms two times before and after exposure under the same condition, dust-blocking performance of the cosmetics is analyzed from changes in an amount of remaining fine dust.

As a result of the test, difference between remaining fine dust between an area where the cosmetics are applied and an area where the cosmetics are not applied can be confirmed as illustrated in FIG. 5. In addition, as indicated in analysis results of FIG. 6, the area of application has the effect of blocking fine dust which is in a statistically significant level ($p<0.05$) compared to the area of non-application.

While the present invention have been described in connection with the exemplary embodiments illustrated in the drawings, it will be appreciated that they are merely an illustrative embodiments and various equivalent modifications and variations of the embodiments can be made by a person having an ordinary skill in the art without departing from the spirit and scope of the present invention. Therefore, the appended claims also include such modifications and variations falling within the true technical scope of the present invention.

What is claimed is:

1. An apparatus for making artificial atmospheric environment including fine dust, the apparatus comprising:
   a chamber in which fine dust is made;
   a wind generation unit including a plurality of driving fans disposed inside the chamber having different angles, the wind generation unit moving supplied dust inside the chamber so that the dust is distributed as actual atmospheric environment in the same or similar manner; and a dust supply unit which is provided integrally with or separately from the chamber to supply fine dust to the chamber,
wherein the plurality of driving fans of the wind generation unit comprises
a corner driving fan disposed at each corner of a bottom surface of the chamber;
a side lower driving fan disposed inward from a bottom surface of facing side surfaces of the chamber;
a central driving fan disposed at a center of a bottom surface of the chamber; and
a side upper driving fan disposed at a central portion or an upper portion of facing side surfaces of the chamber.

2. The apparatus according to claim 1, further comprising: a filter having a backflow prevention filter which prevents air flow from inside to outside the chamber, but allows airflow from outside to inside the chamber.

3. The apparatus according to claim 1, wherein the chamber is formed with an insertion hole to insert arms of a subject on one side, an inlet through which dust is inserted on an upper portion of an upper surface or a side surface, and an outlet at a bottom of a side surface or a lower portion.

4. The apparatus according to claim 3, wherein the insertion hole of the chamber comprises a sealing member to present outflow of fine dust to outside the chamber, and the chamber formed with the insertion hole further comprises a support member to hold arms of a subject.

5. The apparatus according to claim 1, wherein the chamber is made of transparent or semi-transparent acrylic plate.

6. The apparatus according to claim 1, wherein the corner driving fan is disposed at a bottom surface of rectangular corners inside the chamber diagonally to face with each other, and a front direction of the fan is set aside from a central reference point.

7. The apparatus according to claim 1, wherein the corner driving fan comprises a first corner driving fan, a second corner driving fan, a third corner driving fan, and a fourth corner driving fan disposed at a direction in which a front direction of each fan is rotated by 1~15° (θ1) with reference to a center of the chamber.

8. The apparatus according to claim 1, wherein the side lower driving fan is disposed such that a front surface of a fan is disposed to opposite to each other at both sides of the same bottom surface adjacent to a pair of side portions facing each other, and comprises a first side lower driving and a second side lower driving fan disposed at a direction rotated by 1~7° (θ2) with reference to a vertical connection line which connects a pair of side portions of the chamber and a central reference point.

9. The apparatus according to claim 1, wherein the central driving fan is disposed such that a front surface of a fan is placed upward at a center of a bottom surface of the chamber and the fan is disposed to be apart from the bottom surface.

10. The apparatus according to claim 9, wherein the central driving fan comprises a first central driving fan and a second central driving fan which are disposed to be apart from each other at a predetermined distance.

11. The apparatus according to claim 9, wherein the central driving fan generates convection, inhales dust at a bottom portion, and sends dust to an upper portion.

12. The apparatus according to claim 1, wherein the side upper driving fan is disposed such that a front surface of a fan is disposed to be opposite to each other at a pair of central or upper portions facing with each other of the chamber, and comprises a first side upper driving fan and a second side upper driving fan disposed at a direction rotated by 1~50° (θ3) with reference to a vertical connection line which connects a pair of side portions of the chamber and a central reference point.

13. The apparatus according to claim 1, wherein the dust supply unit comprises carbon black as a material of the fine dust.

14. An analysis system for dust blocking of cosmetics using an apparatus for making artificial atmospheric environment, the system comprising:
a capturing device which captures a target which is applied with cosmetics and a target which is not applied with cosmetics before and after exposure to fine dust;
an apparatus for making artificial atmospheric environment which exposes the target to fine dust; and
an image analysis device which compares and analyzes images of the targets captured before and after exposure to fine dust,
the apparatus for making artificial atmospheric environment comprising:
a chamber in which fine dust is made;
a wind generation unit including a plurality of driving fans disposed inside the chamber having different angles, the wind generation unit moving supplied dust inside the chamber so that the dust is distributed as actual atmospheric environment in the same or similar manner; and
a dust supply unit which is provided integrally with or separately from the chamber to supply fine dust to the chamber.

15. The system according to claim 14, wherein the apparatus drives each driving fan provided inside the chamber for 20-40 seconds, and wherein carbon black is input in an environment where wind speed is kept to 2.5~3 m/s, and concentration of fine dust by the carbon black is 200~3,000 mg/m3.

16. The system according to claim 14, wherein the analysis device, which is interlocked with the capturing device, receives images captured before and after exposure to fine dust through an image receiving unit, converts the received images to an editable image file thorough a conversion unit, and measures and analyzes fine dust amount from the converted image file.

17. The system according to claim 16, wherein the analysis device applies counting statistics to measure and analyze the fine dust amount, reach measurement results by setting an intensity range, and analyze an intensity range by overlapping a same part between a part before exposure and a part after exposure.

18. The system according to claim 14, wherein the plurality of driving fans of the wind generation unit comprises
a corner driving fan disposed at each corner of a bottom surface of the chamber.

19. The system according to claim 18, wherein the plurality of driving fans of the wind generation unit further comprises
a side lower driving fan disposed inward from a bottom surface of facing side surfaces of the chamber;
a central driving fan disposed at a center of a bottom surface of the chamber; and
a side upper driving fan disposed at a central portion or an upper portion of facing side surfaces of the chamber.

20. The system according to claim 14, wherein the plurality of driving fans of the wind generation unit is configured to generate an air flow that is reinforced, offset, or changed by each of said plurality of driving fans.

* * * * *